US012800604B2

(12) United States Patent
Kim et al.

(10) Patent No.: US 12,800,604 B2
(45) Date of Patent: Nov. 17, 2026

(54) IN VITRO DIAGNOSTIC APPARATUS

(71) Applicant: BODITECH MED INC., Gangwon-Do (KR)

(72) Inventors: Byeong Chul Kim, Gangwon-Do (KR); Young Duk Kim, Gangwon-do (KR); Min Whan Lee, Gangwon-do (KR); Soon Il Kwon, Gangwon-do (KR); Uk Bin Im, Gangwon-Do (KR); Youn Tae Im, Gangwon-do (KR); Jeong Ae Shin, Gangwon-do (KR); Ju Hyoung Bang, Gangwon-do (KR)

(73) Assignee: BODITECH MED INC., Gangwon-Do (KR)

( * ) Notice: Subject to any disclaimer, the term of this patent is extended or adjusted under 35 U.S.C. 154(b) by 1025 days.

(21) Appl. No.: 17/734,184

(22) Filed: May 2, 2022

(65) Prior Publication Data

US 2022/0373571 A1 Nov. 24, 2022

(30) Foreign Application Priority Data

May 21, 2021 (KR) ........................ 10-2021-0065755

(51) Int. Cl.
*G01N 1/14* (2006.01)
*G01N 1/38* (2006.01)
(Continued)

(52) U.S. Cl.
CPC ............... *G01N 35/10* (2013.01); *G01N 1/14* (2013.01); *G01N 1/38* (2013.01); *G01N 21/03* (2013.01);
(Continued)

(58) Field of Classification Search
CPC ............ G01N 35/10; G01N 1/14; G01N 1/38; G01N 21/03; G01N 21/78; G01N 33/521;
(Continued)

(56) References Cited

U.S. PATENT DOCUMENTS 5,360,739 A * 11/1994 Fan .......................... G01N 1/30 436/63
2005/0196867 A1* 9/2005 Bower ............ G01N 35/00603 436/43
(Continued)

FOREIGN PATENT DOCUMENTS

EP 3534140 A1 9/2019
KR 101811786 B1 12/2017
(Continued)

OTHER PUBLICATIONS

WO2015172971 English Translation (Year: 2015).*

*Primary Examiner* — Charles Capozzi
*Assistant Examiner* — Michael Stanley Gzybowski
(74) *Attorney, Agent, or Firm* — Klintworth & Rozenblat LLP

(57) ABSTRACT

The present invention relates to an automatic in vitro diagnostic apparatus capable of automatically performing a series of examination processes including a pretreatment process for specific components included in a biological sample such as blood and urine. The apparatus of the present invention comprises a base frame 104; a cuvette tray 110 movable back and forth on the base frame 104, for mounting cuvette holders 10 accommodating a plurality of cuvettes arranged thereon alongside each other; a tube tray 120 movable back and forth on the base frame, for mounting tube holders 20 accommodating a plurality of sample tubes containing samples thereon; and a sampling operation unit 500 movable left and right on the base frame 104, for mixing a sample contained in the sample tube with a reagent, and dropping the mixed solution onto an analysis strip provided in the cuvette.

8 Claims, 14 Drawing Sheets

(51) Int. Cl.

| | |
|---|---|
| ***G01N 21/03*** | (2006.01) |
| ***G01N 21/78*** | (2006.01) |
| ***G01N 33/52*** | (2006.01) |
| ***G01N 35/10*** | (2006.01) |
| *G01N 21/77* | (2006.01) |
| *G01N 35/00* | (2006.01) |

(52) U.S. Cl.

CPC ........... *G01N 21/78* (2013.01); *G01N 33/521* (2013.01); *G01N 2021/7759* (2013.01); *G01N 2035/00465* (2013.01)

(58) Field of Classification Search

CPC . G01N 2021/7759; G01N 2035/00465; G01N 21/8483; G01N 2035/00524; G01N 2035/0436; G01N 35/04; G01N 35/1079; G01N 35/1083; G01N 2035/00108; G01N 2035/00752; G01N 2035/00831; G01N 2035/0413; G01N 2035/103; G01N 35/00029; G01N 21/01; G01N 35/1081; G01N 35/026; G01N 35/1002; G01N 2035/00534

See application file for complete search history.

(56) References Cited

U.S. PATENT DOCUMENTS

| | | | | |
|---|---|---|---|---|
| 2013/0183769 | A1 | 7/2013 | Tajima | |
| 2017/0269112 | A1* | 9/2017 | Gerstel | G01N 35/1079 |
| 2018/0074027 | A1 | 3/2018 | Kim et al. | |

FOREIGN PATENT DOCUMENTS

| | | | | |
|---|---|---|---|---|
| WO | WO-2011011075 | A2 * | 1/2011 | G01N 35/00722 |
| WO | WO-2015172971 | A1 * | 11/2015 | G06T 7/0008 |
| WO | 2017204274 | A1 | 11/2017 | |
| WO | 2020005789 | A1 | 1/2020 | |

* cited by examiner

IN VITRO DIAGNOSTIC APPARATUS

FIELD OF THE INVENTION

The present invention relates to an automatic in vitro diagnostic apparatus capable of automatically performing a series of examination processes, including a pretreatment process for specific components included in a biological sample such as blood and urine.

BACKGROUND OF THE INVENTION

With the recent increase in human-animal infections, the epidemic of new influenza, and various other infections, increasing a lot is the demand for examining the presence or absence of disease and the state of the disease by analyzing the changes that occur after reacting biological samples, such as blood and urine collected from humans or animals, with predetermined reagents.

In this sample diagnosis process, it is very important for obtaining reproducible results that samples and reagents used for examining the samples are not affected by external factors, and that the accurate amounts of them are used each time. In the course of the examination, since the sample and the reagent may be exposed to the outside, it is necessary to effectively prevent the contamination caused by exposure of the sample and the reagent, and to secure the accuracy of the examination by using the accurate amounts.

In addition, it is also necessary to reduce the steps included in the overall examination and the spent cost by making the examination for detection and reading/analysis of the reaction product be performed accurately and quickly in one integrated system after the reaction of the reagent and the sample, thereby cutting examination time and examination cost down.

Furthermore, since a conventional in vitro diagnostic apparatus used for such an examination uses only one diagnostic kit for one diagnostic examination, it is limited in rapidly examining, analyzing and diagnosing a target object.

TECHNICAL CHALLENGE

The present invention intends to solve the problems of the prior art, and provides an automatic in vitro diagnostic apparatus that simultaneously performs multiple types of examinations on a single sample or performs a large number of samples at the same time by automating all of the series of examination processes from sample collection to sample pretreatment, so that it can quickly and accurately perform the examination process.

Technical Solutions

The present invention for achieving the above-mentioned objectives provides a automatic in vitro diagnostic apparatus comprising: a base frame; a cuvette tray movable back and forth on the base frame for mounting cuvette holders thereon, the cuvette holders accommodating a plurality of cuvettes arranged alongside, wherein one unit set of the cuvette includes at least one open chamber, a reagent chamber, a tip, and a cartridge comprising an assay strip; a first driving unit for moving the cuvette tray back and forth; a tube tray movable back and forth in parallel with the moving direction of the cuvette tray on the base frame for mounting tube holders thereon, the tube holders accommodating a plurality of sample tubes containing samples; a second driving unit for moving the tube tray back and forth; a sampling operation unit movable left and right on the base frame for collecting a sample contained in the sample tube and mixing it with a reagent, and dropping the mixed solution onto an assay strip provided in the cuvette; a third driving unit for moving the sampling operation unit left and right; an optical analysis unit disposed at the rear end of the sampling operation unit, movable left and right on the base frame, for optically analyzing the assay strip of the cuvette; and a fourth driving unit for moving the optical analysis unit left and right.

Effects of the Invention

An automatic in vitro diagnostic apparatus according to the present invention comprises: a cuvette tray for mounting cuvette holders accommodating a plurality of cuvettes arranged alongside thereon so as to be movable back and forth in the apparatus, a tube tray for mounting tube holders accommodating a plurality of sample tubes thereon so as to be movable back and forth in the apparatus, and a mixing unit for mixing the sample contained in the sample tube, so that samples in tubes may be directly put into the apparatus and a series of inspection tasks including the sample pretreatment process may be all automatically performed, thereby minimizing the contamination caused by exposing the samples to the outside and thereby improving the accuracy and reproducibility of the examination.

In addition, according to the present invention, a cuvette holder for accommodating a plurality of cuvettes arranged alongside, and a tube holder for accommodating a plurality of capless tubes are directly put into the apparatus and then the examination is performed, so that it is possible to perform an examination for a large number of samples for one examination item or to perform an examination (analysis) for one sample for multiple examination items in one apparatus at the same time.

DETAILED DESCRIPTION OF EXEMPLARY EMBODIMENT OF THE INVENTION

Specific structural or functional descriptions presented in the embodiments of the present invention are only exemplified for the purpose of describing embodiments according to the concept of the present invention, and the embodiments according to the concept of the present invention may be implemented in various forms. In addition, the present invention should not be construed as being limited to the embodiments described herein, and it should be understood to include all modifications, equivalents and substitutes that belong to the spirit and scope of the present invention.

Meanwhile, in the present invention, terms such as first and/or second may be used to describe various components, but the components are not limited to the terms. The above terms are used only for the purpose of distinguishing one component from other components, for example, within the scope not departing from the claims according to the concept of the present invention, the first component may be named as the second component, Similarly, the second component may also be referred to as a first component.

When a component is referred to as being “connected to” or “in contact with” another component, it should be understood that a component may be directly or indirectly connected to or in contact with another component so other component(s) may exist between them in their connection or contact. On the other hand, when a component is referred to as being “directly connected to” or “in direct contact with” another component, it should be understood that no other component exists between them. Other expressions for describing the relationship between components, such as, “between” and “immediately between” or “adjacent to” and “directly adjacent to”, etc., should be interpreted in the same way.

The terms used herein are used only to describe specific embodiments, and are not intended to limit the present invention. The singular expression includes the plural expression unless the context clearly dictates otherwise. In the present specification, terms such as “comprise”, “include” or “have” are intended to designate the existence of an embodied feature, number, step, operation, component, part, or combination thereof, and it should be understood that the existence or addition of one or more other features, numbers, steps, operations, components, parts or combinations thereof is not precluded in advance.

Hereinafter, the present invention will be described in detail with reference to the accompanying drawings.

Figure 1:
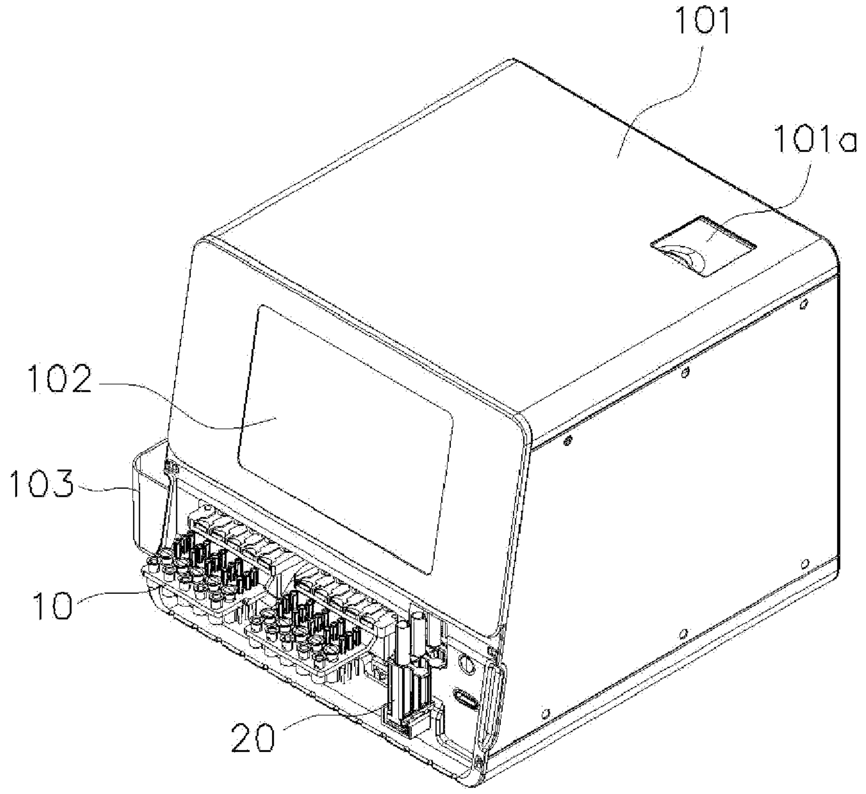
FIG. 1 is a perspective view illustrating an automatic in vitro diagnostic apparatus according to an embodiment of the present invention.
Figure 2:
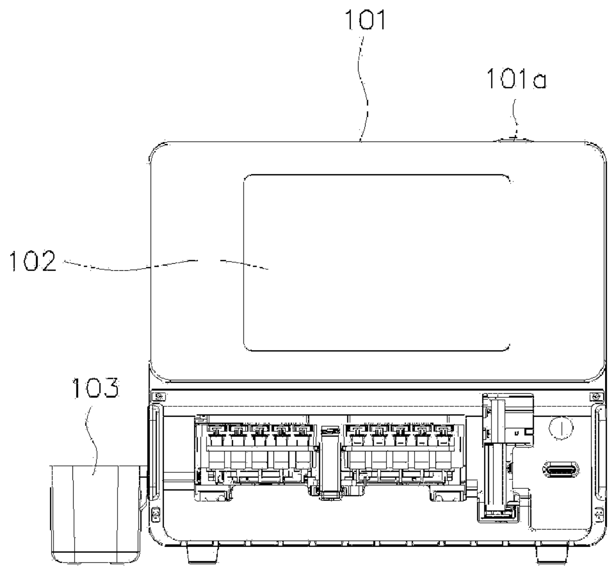
FIG. 2 is a front view illustrating an automatic in vitro diagnostic apparatus according to an embodiment of the present invention.

FIGS. 1 and 2 are a perspective and front view, respectively, illustrating the appearance of an automatic in vitro diagnostic apparatus according to an embodiment of the present invention.

Referring to FIGS. 1 and 2, the automatic in vitro diagnostic apparatus of this embodiment is provided with a touch screen 102 for outputting the operation of the device and the analysis results on the front part of the housing 101 constituting the appearance, a first inlet into which the cuvette holders 10 are inserted under the touch screen 102, and a second inlet into which the tube holder 20 is inserted in parallel with the first inlet. In this embodiment, it is shown that the cuvette holders 10 are placed in two rows, and each cuvette holder 10 has the same structure, but they can be moved forward and backward independently of each other. In the following description, since both of the cuvette holders 10 placed in two rows have the same structure, only one reference numeral is used without a separate distinction. Although, in the present embodiment, the cuvette holders 10 are illustrated as being placed in two rows, they may be placed in more rows. In addition, this embodiment may further comprise a buffer tube holder 30 (see FIG. 3) between the two rows of the cuvette holders 10. The buffer tube holder 30 accommodates a plurality of buffer tubes containing a buffer solution for diluting granules, and such a buffer tube holder 30 can be moved back and forth by a separate driving unit. On the other hand, the buffer tube holder 30 may further accommodate a pretreatment tube containing pretreatment solution as well as the buffer tube.

A tip collection container 103 for collecting the tips after use may be provided at the side of the housing 101. A tip removal unit 107 (see FIG. 3) for removing the tip after use is provided on the upper portion of the tip collection container 103. The tip removal unit 107 has a tip removal hole 107*a* formed with an opening at the top. The tip removal unit 107 removes the tip 13 mounted on the tip adapter of the sampling operation unit. This will be described again in the related drawings. The housing 101 may include a printer 101*a* that outputs the diagnosis result as a printout on the upper portion of the housing 101.

Figure 3:
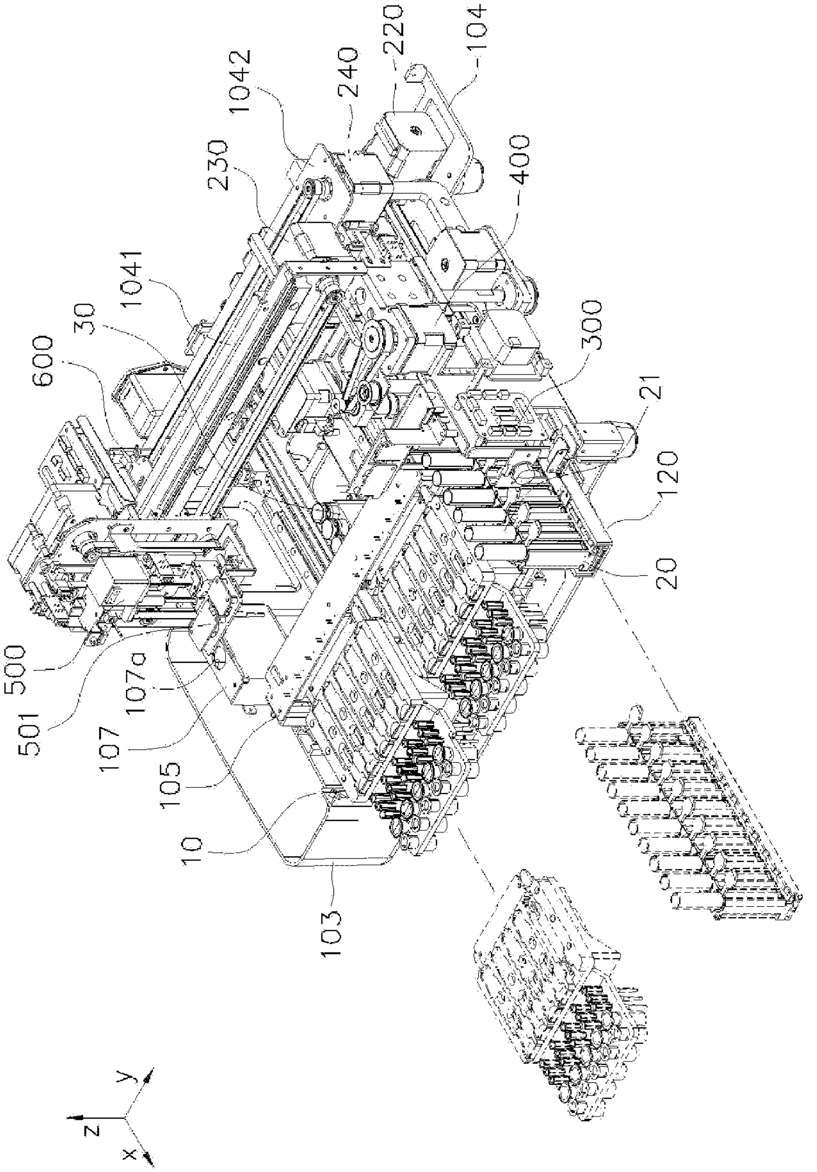
FIG. 3 is a perspective view illustrating an automatic in vitro diagnostic apparatus without its housing according to an embodiment of the present invention.
Figure 4:
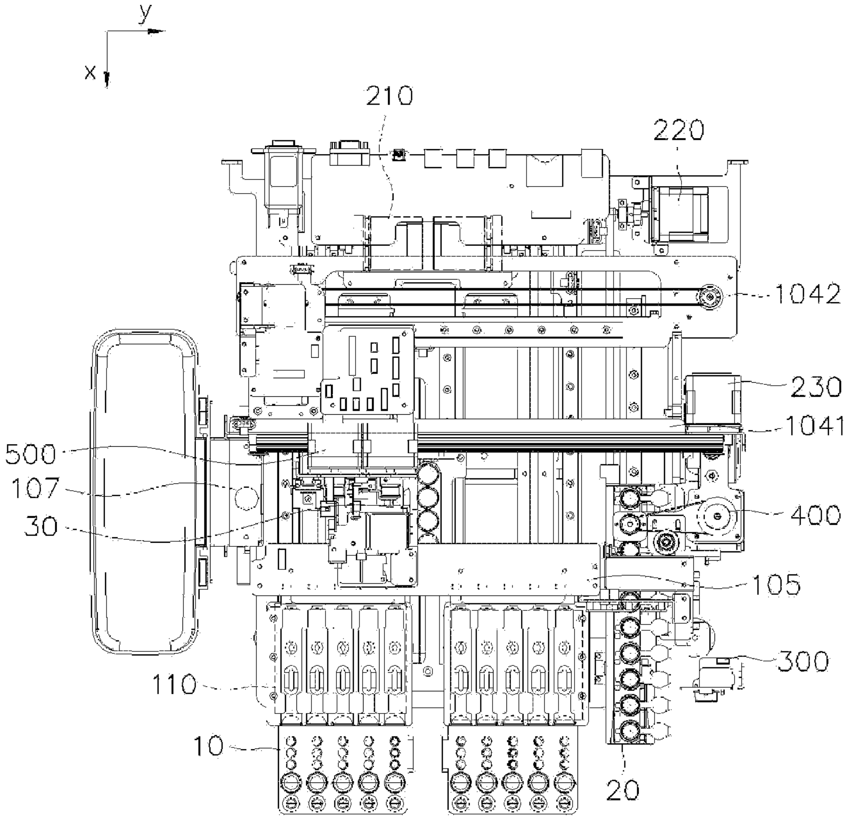
FIG. 4 is a top view illustrating an automatic in vitro diagnostic apparatus without its housing according to an embodiment of the present invention.

FIGS. 3 and 4 are perspective and top views, respectively, illustrating an automatic in vitro diagnostic apparatus without its housing according to an embodiment of the present invention.

Referring to FIGS. 3 and 4, the automatic in vitro diagnostic apparatus of this embodiment comprises a base frame 104, a cuvette tray 110 and a tube tray 120 that are provided to be movable in the front-rear direction (x-axis direction) on the base frame 104, a sampling operation unit 500 and an optical analysis unit 600 that are provided to be movable in the left-right direction (y-axis direction) on the base frame 104, and a plurality of driving units 210, 220, 230, and 240 for driving each component. Preferably, the automatic in vitro diagnostic apparatus of this embodiment further comprises: a code recognition unit 300 fixed to the base frame 104, for recognizing code information attached to the sample tube, and a mixing unit 400 fixed to the base frame 104, for mixing the sample contained in the sample tube. Note that it should be understood that the term ‘moving direction’ is used to describe the front-rear direction (x-axis direction) with respect to the horizontal plane in which the cuvette tray 110 and the tube tray 120 are located, and the direction perpendicular to the ‘moving direction’ describes the left-right direction (y-axis direction) for the convenience of spatial explanation, respectively.

The base frame 104 comprises members for supporting main components or guiding the moving direction of various moving components, and may comprise a combination of a plurality of panels, or a guide member for guiding the moving direction of the moving components. It is not limited to a specific structure or form.

Specifically, the cuvette tray 110 and the tube tray 120 are movable in the front-rear direction (x-axis direction) on the base frame 104, and the base frame 104 may have guide rails for guiding the cuvette tray 110 and the tube tray 120 in the front-rear direction.

The cuvette tray 110 and the tube tray 120 are moved back and forth by the first driving unit 210 and the second driving unit 220 provided on the base frame 104. The first driving unit 210 and the second driving unit 220 may be electric motors that supply driving force through the cuvette tray 110, the tube tray 120, and a caterpillar type belt. According to the rotation direction of each electric motor, the cuvette tray 110 and the tube tray 120 can be precisely positioned in the front-rear direction (x-axis). Meanwhile, in order to achieve precise position control of the cuvette tray 110 and the tube tray 120, each driving unit may further have an encoder or a position detection sensor for position control.

The sampling operation unit 500 and the optical analysis unit 600 are movable in the left-right direction (y-axis direction) on the base frame 104.

A first upper frame 1041 and a second upper frame 1042 are installed on the base frame 104 in the left-right direction at a predetermined height of the front-rear moving section of the cuvette tray 110 and the tube tray 120, so that the sampling operation unit 500 and the optical analysis unit 600 may be moved in the left-right direction according to each of upper frames 1041 and 1042.

The sampling operation unit 500 and the optical analysis unit 600 move left and right by the third driving unit 230 and the fourth driving unit 240 provided on the first upper frame 1041 and the second upper frame 1042. The third driving unit 230 and the fourth driving unit 240 are electric motors that supply driving force through the sampling operation unit 500 and the optical analysis unit 600, and a caterpillar type belt. According to the rotation direction of each electric motor, the sampling operation unit 500 and the optical analysis unit 600 can be precisely positioned in the left-right direction (y-axis direction). Meanwhile, in order to achieve precise position control of the sampling operation unit 500 and the optical analysis unit 600, each driving unit may further have an encoder or a position detection sensor for position control. In addition, in the present embodiment, each of the driving units 210, 220, 230, and 240 exemplifies that the driving force of the electric motor is transmitted through a belt, but the present invention is not limited to the present embodiment, and various well-known driving force transmitting means such as a linear driving unit may be used.

Preferably, the sampling operation unit 500 may further comprise a camera module 501 for taking an image. The camera module 501 detects image information while moving horizontally together with the sampling operation unit 500, so as to identify cartridge information, tips, and the presence or absence of a buffer tube.

Reference numeral 105 denotes a PCB that has a barcode reader provided on the upper portion of the front-rear moving section of the cuvette tray 110, for recognizing barcodes of each cuvette disposed in the cuvette holder 10.

The code recognition unit 300 is adjacent to the tube tray 120 and identifies the code information attached to the tube holder 20 and/or each sample tube 21 accommodated in the tube holder 20. This code information includes information about the sample, and may be provided by a barcode or QR code. On the other hand, it may further comprise a separate camera adjacent to the code recognition unit 300, and such a camera can be used for determining the type (size) of the tube accommodated in the tube holder 20.

Hereinafter, each detailed configuration will be described in detail with reference to the related drawings.

The cuvette tray 110 is a member on which the cuvette holder 10 is seated, and preferably, the cuvette tray 110 may further comprise a temperature control unit for maintaining the seated cuvette holder 10 at a temperature of a predetermined condition. For example, such a temperature control unit may be provided by a known Peltier element and a fan capable of temperature control, but is not limited thereto. Known temperature control devices can be used within a range capable of controlling the temperature of the cuvette holder and maintaining a constant temperature. On the other hand, the cuvette holder 10 and the cuvette tray 110 may be integrated into each other, or the cuvette holder 10 and the cuvette tray 110 may be detachable from each other. In this cuvette holder 10, a plurality of cuvettes for mixing and reacting a sample and a reagent are arranged alongside, and each cuvette includes a reagent, a tip, and an assay strip required for examination.

Figure 5:
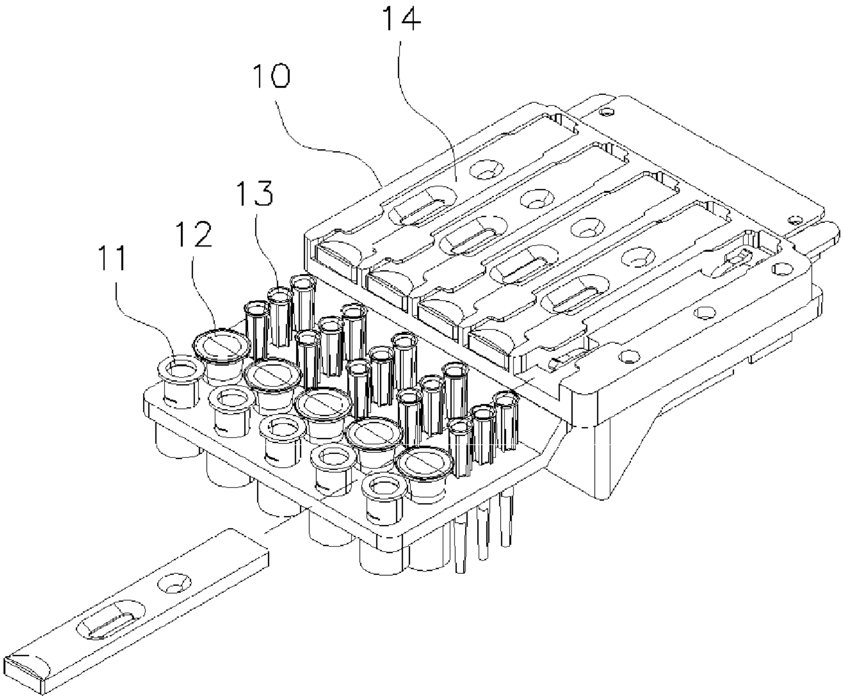
FIG. 5 is a perspective view illustrating a cuvette holder according to an embodiment of the present invention.

FIG. 5 shows a cuvette holder according to an embodiment of the present invention.

Referring to FIG. 5, the cuvette holder 10 is configured to arrange a plurality of cuvettes alongside each other, wherein each cuvette includes at least one open chamber 11, a reagent chamber 12, at least one tip 13, and a cartridge 14 comprising an assay strip. In the open chamber 11, a sample is dispensed to be mixed with a reagent, and the reagent chamber 12 is filled with a reagent, such as an antibody, to react with the sample. The reagent chamber 12 is generally provided sealed with a sealing paper (aluminum foil), and the sealing paper needs to be removed for examination. In the present invention, the sealing paper of the reagent chamber 12 can be removed in the diagnostic apparatus, and a detailed description thereof will be described again in the related drawings.

The cartridge 14 includes an assay strip where a mixture of sample and reagent is dripped to react. However, the number of chambers and tips of the cuvette holder 10 can be changed according to the type of examination. For example, each row of the cuvette holder 10 may accommodate different examination cuvettes from those of other rows of the cuvette holder 10, so that various examinations can be performed on one sample at the same time, or all the rows of the cuvette holder 10 accommodate the same examination cuvettes so that the same examinations can be performed on multiple samples at the same time. The same test can be performed on dog samples at the same time. Each cuvette (cartridge) may include a barcode (QR code) containing information on the sample or reagent.

While, in this embodiment, each chamber and the cartridge 14 including the assay strip are separately disposed in the cuvette holder, an integral type of cuvette may be used too. For example, this integral type of cuvette may be provided by a multi-well cuvette disclosed in Korean Patent Publication No. 10-1661098 (published on Sep. 29, 2016) of the present applicant.

Figure 14:
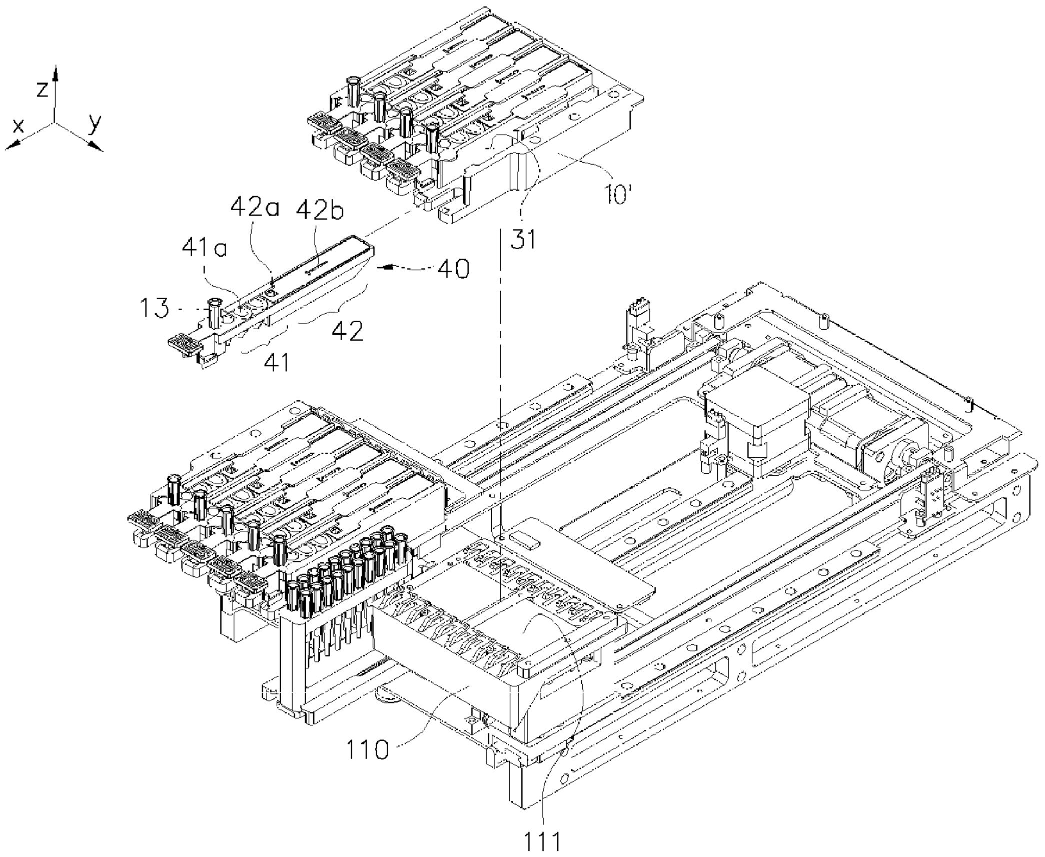
FIG. 14 is a perspective view of a main part of an automatic in vitro diagnostic apparatus according to another embodiment of the present invention.

FIG. 14 is a perspective view showing configuration of a main part of an automatic in vitro diagnostic apparatus according to another embodiment of the present invention. It shows an automatic in vitro diagnostic apparatus employing a multi-well cuvette, and the same reference numerals are used for the same components as in the previous embodiment.

Referring to FIG. 14, the cuvette tray 110 includes a temperature control unit 111, and a cuvette holder 10' is mounted on and fastened to the upper end of the temperature control unit 111. In the present embodiment, the cuvette holder 10' comprises five rows of slots 31 each accommodating a multi-well cuvette 40. The number of slots 31 can be increased or decreased. The multi-well cuvette 40 has a multi-well structure having a plurality of wells and barriers for separating the wells from one another to prevent reagents and samples from being mixed with each other. The multi-well cuvette 40 includes at least one tip 13, a reaction chamber 41 having a plurality of chambers 41*a* for containing a sample and a reagent, and a detection unit 42 for detecting a reaction between the sample and the reagent. The detection unit 42 comprises a chromatographic analysis means suitable for chromatographic analysis of the reaction product that is made by reacting the sample and the reagent in the reaction chamber unit 100. In addition, the detection unit 42 includes a sample inlet 42*a* and the measurement window 42*b*. The detection unit 42 may include a means suitable for chromatographic analysis of the reactant, for example, lateral flow analysis. Preferably, the detection unit 42 may include a cartridge for a lateral flow analysis. Reference numerals 42*a* and 42*b* denote a sample inlet and a measurement window of the cartridge, respectively.

Figure 6:
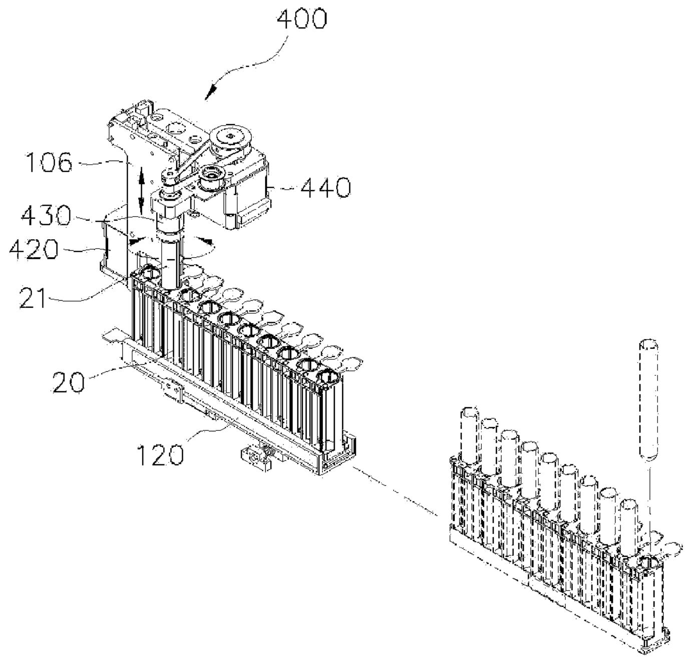
FIG. 6 is a perspective view illustrating a mixing unit according to an embodiment of the present invention.
Figures 7A, 7B, 7C:
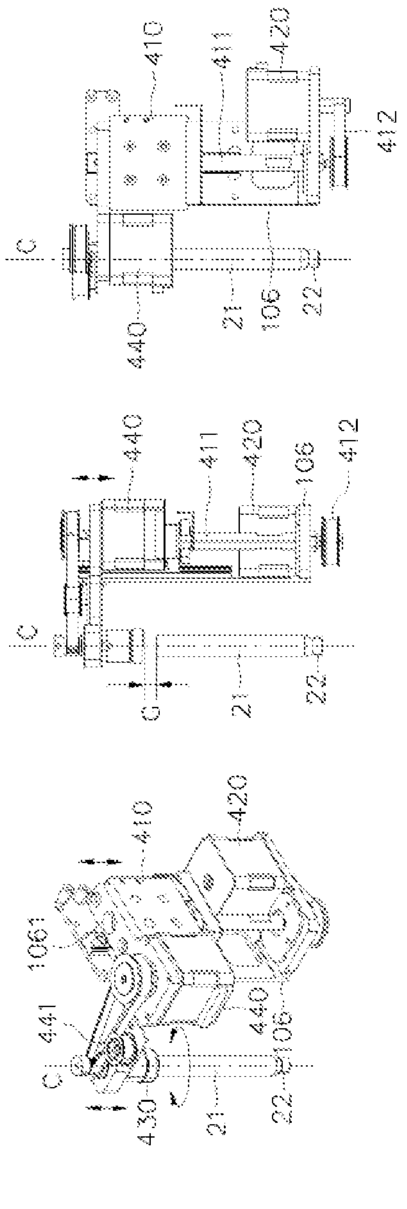
FIGS. 7*a*, 7*b* and 7*c* are perspective, side and front views, respectively, illustrating a mixing unit respectively according to an embodiment of the present invention.

FIG. 6 is a perspective view illustrating a mixing unit according to an embodiment of the present invention. FIGS. 7*a*, 7*b* and 7*c* are perspective, side and front views, respectively, illustrating a mixing unit respectively according to an embodiment of the present invention.

Referring to FIGS. 6 and 7, the tube holder 20 accommodates a plurality of sample tubes 21 alongside, and the sample tubes 21 are seated on the tube tray 120 so that the sample of each sample tube 21 may be examined in a series of processes. Preferably, the sample tube 21 is a capless tube.

The mixing unit 400 mixes the sample (eg, blood) of each sample tube 21. The mixing unit comprises: a fixing bracket 106 fixed to the base frame; an elevating module 410 supported by the fixing bracket 106 so as to move up and down; a fifth driving unit 420 for driving the elevating module 410 up and down; a fixing head 430 supported by the elevating module 410 so as to be able to rotate, and capable of getting fixed closely to an upper opening end of the sample tube 21; and a sixth driving unit 440 provided for the elevating module 410, for rotating the fixing head 430.

The fixing bracket 106 is provided with a guide rail 1061 in vertical direction, and the elevating module 410 is assembled with the guide rail 1061 to vertically move by the fifth driving unit 420.

The elevating module 410 is provided with a linear driving unit 411. The linear driving unit 411 transmits a driving force via the fifth driving unit 420 and the belt 412 to the fifth driving unit 420. The elevating module 410 is moved up and down by forward or reverse rotation of the fifth driving unit 420.

The fixing head 430 is supported by the elevating module 410 so as to freely rotate in a rotation axis direction (C), and is fixed in close contact with the upper open end of the sample tube 21. Preferably, the fixing head 430 may further include a contact pad having elasticity in order to increase the adhesion to the lower contact end that is in direct close contact with the sample tube 21, The material of the contact pad may be a rubber material having elasticity.

The fixing head 430 is rotationally driven by the sixth driving unit 440 fixed to the elevating module 410. In the present embodiment, the sixth driving unit 440 comprises an electric motor that rotates the driving shaft of the fixing head 430 through a belt. Reference numeral 441 denotes a tension control pulley for adjusting the tension of the belt. In the present embodiment, the sixth driving unit 440 has an electric motor that rotates the driving shaft of the fixing head 430 through a belt.

The mixing unit 400 configured as described above mixes the sample contained in the sample tube 21 as follows. The sample tube 21 is horizontally moved to the initial position where the sample tube 21 is aligned in parallel with the rotation axis direction (C) of the fixing head 430. Then, the top of the sample tube 21 is spaced apart from the fixing head 430 with a predetermined gap (G) between them. Thereafter, as the elevating module 410 is moved down by the fifth driving unit 420, the fixing head 430 comes into close contact with the upper opening end of the sample tube 21. Next, as the fixing head 430 and the sample tube 21 are turned (rotated) together by the torque of the sixth driving unit 440, the samples get mixed.

Reference numeral 22 is a member provided in the tube holder to support the lower end of the sample tube 21 to assist the rotational movement of the sample tube 21.

Figure 8:
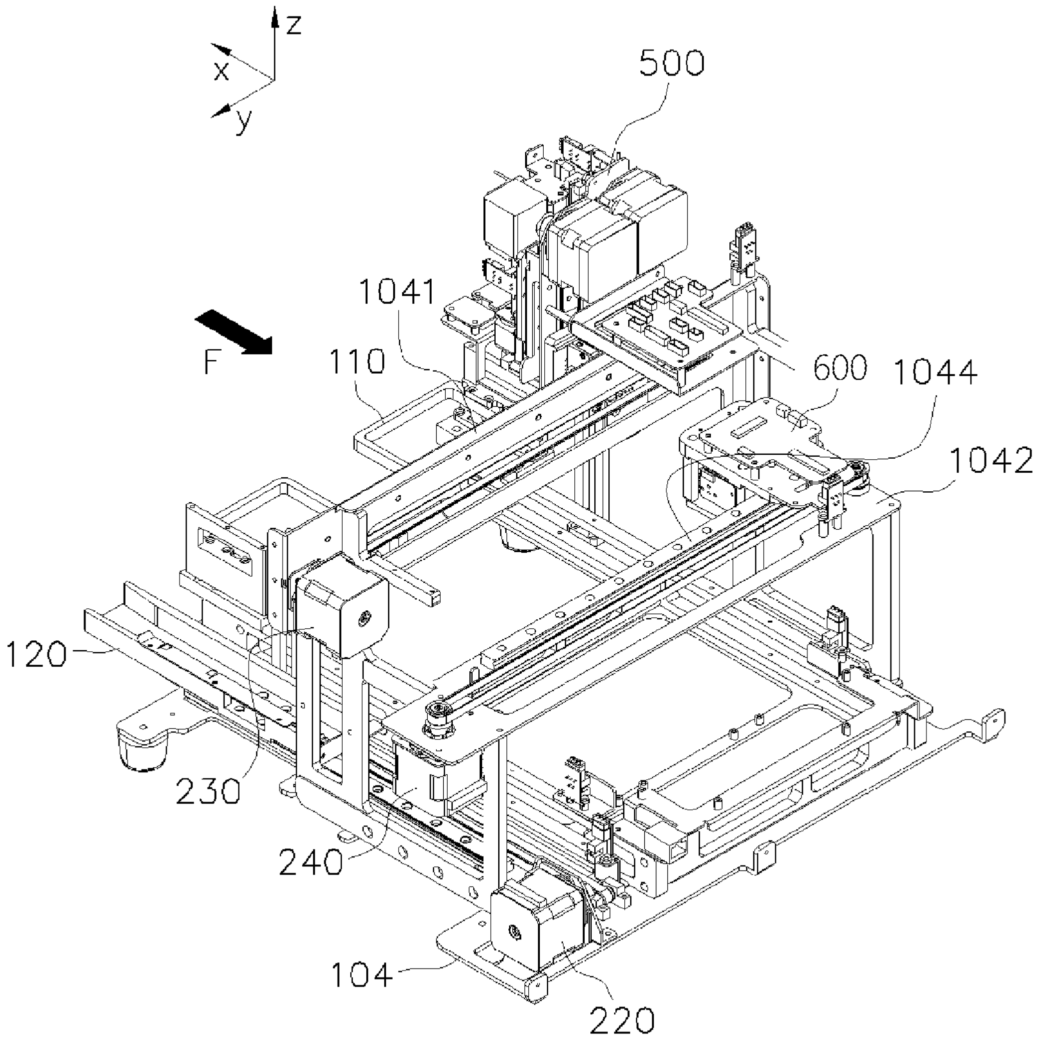
FIGS. 8 and 9 are perspective views illustrating a sampling operation unit and an optical analysis unit, respectively, according to an embodiment of the present invention.
Figure 9:
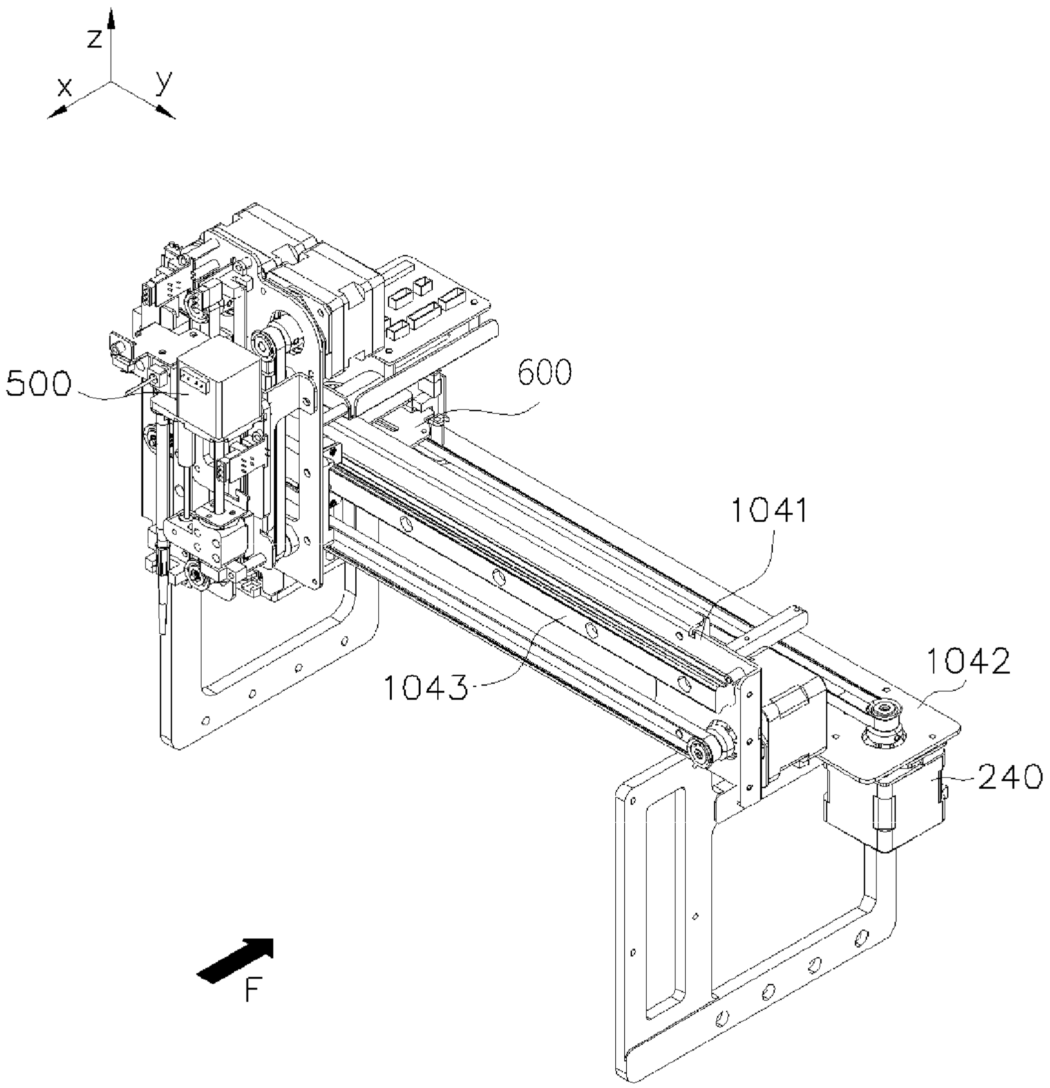

FIGS. 8 and 9 are perspective views illustrating a sampling operation unit and an optical analysis unit respectively according to an embodiment of the present invention, and omit other components except the sampling operation unit and the optical analysis unit for a better understanding. Arrow F indicates the insertion direction of the cuvette holder.

Referring to FIGS. 8 and 9, the sampling operation unit 500 is provided to be movable along the first upper frame 1041 installed in the left-right direction at a predetermined height above the base frame 104. The first upper frame 1041 has a first guide beam 1043 in the longitudinal direction. The sampling operation unit 500 is assembled with the first guide beam 1043 and is movable in the left-right direction (y-axis direction) along the first upper frame 1041. A third driving unit 230 is fixed to one side of the first upper frame 1041. The drive shaft of the third driving unit 230 is connected to a belt, and the sampling operation unit 500 is fixed to the belt. The sampling operation unit 500 is controlled to be positioned in the left-right direction (y-axis direction) by the forward or reverse rotation of the third driving unit 230.

The optical analysis unit 600 is provided to be movable along the second upper frame 1042 installed in the left-right direction at a predetermined height above the base frame 104. The second upper frame 1042 has a second guide beam 1044 in the longitudinal direction. The optical analysis unit 600 is assembled with the second guide beam 1044 and is movable in the left-right direction (y-axis direction) along the second upper frame 1042. A fourth driving unit 240 is fixed to one side of the second upper frame 1042. The drive shaft of the fourth driving unit 240 is connected to a belt, and the optical analysis unit 600 is fixed to the belt. The optical analysis unit 600 is controlled to be positioned in the left-right direction (y-axis direction) by the forward or reverse rotation of the fourth driving unit 240.

The optical analysis unit 600 generates data by reading the reaction result detected by the assay strip of each cuvette, so that qualitative and/or quantitative results of a specific target analyte included in the sample may be obtained using the generated data.

Figure 10:
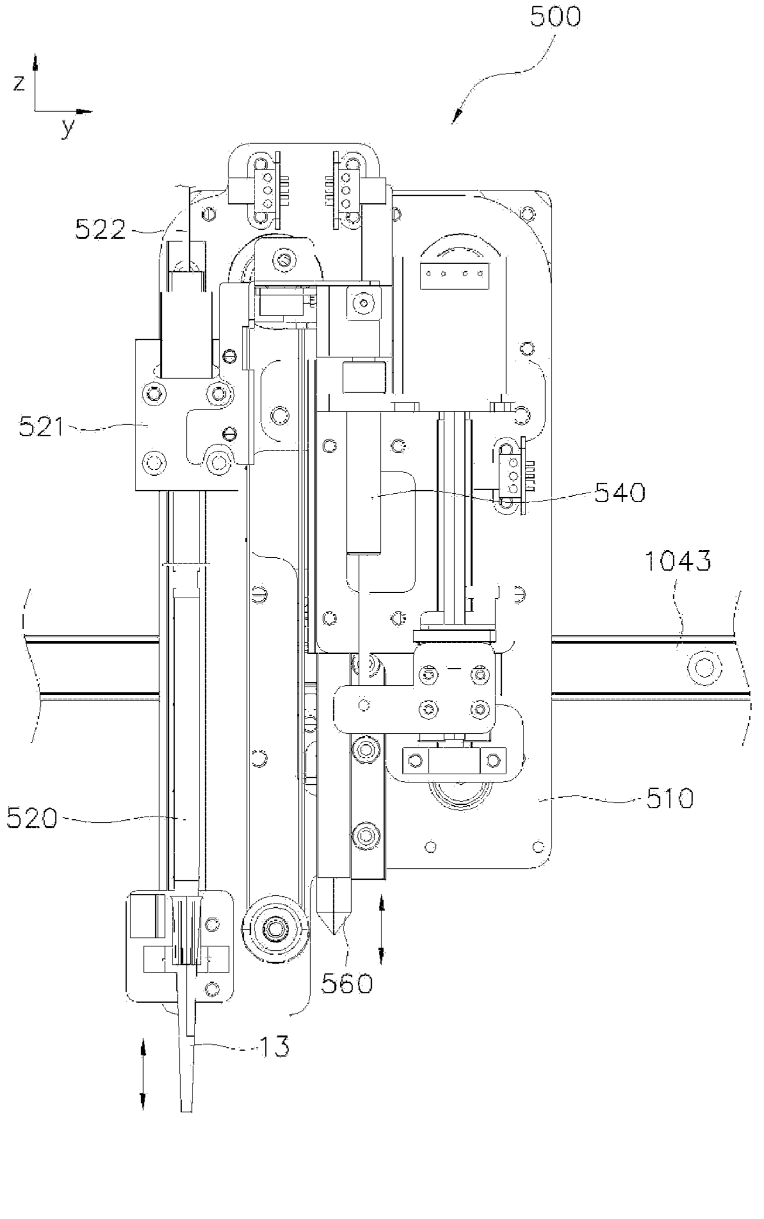
FIG. 10 is a front view illustrating a sampling operation unit according to an embodiment of the present invention.
Figure 11B:
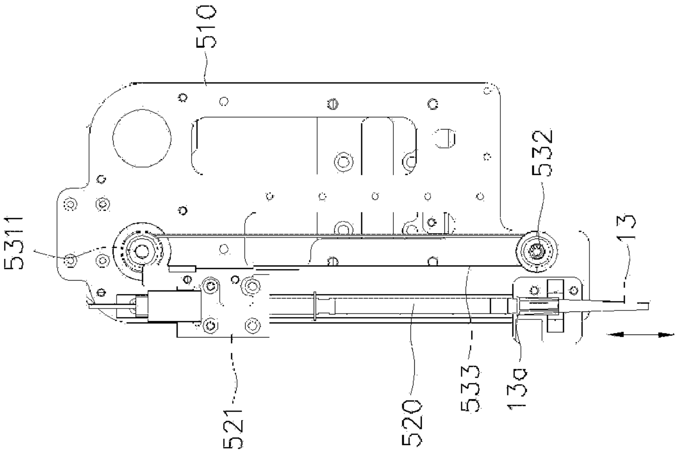
FIGS. 11*a* and 11*b* are perspective and front views, respectively, illustrating the sampling operation unit without some components (pump unit) according to an embodiment of the present invention.
Figure 11A:
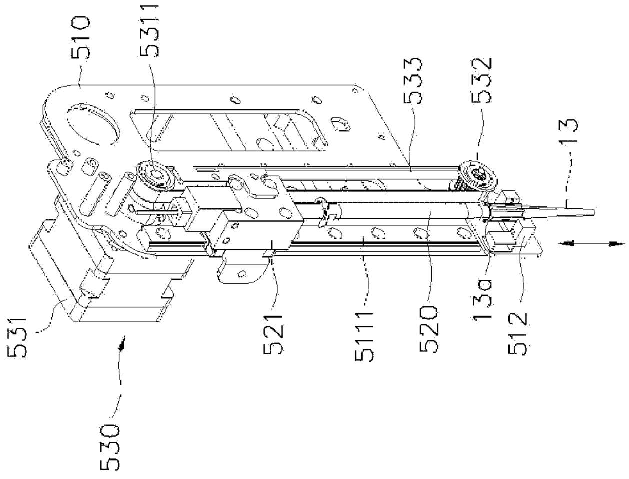
Figure 12B:
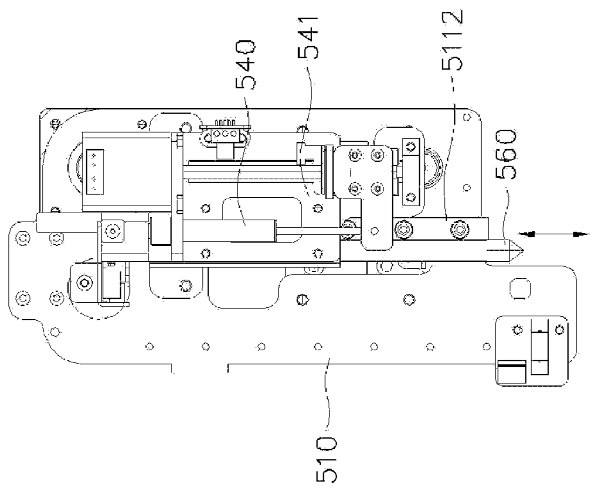
FIGS. 12*a* and 12*b* are perspective and front views, respectively, illustrating the sampling operation unit without some components (tip adapter unit) according to an embodiment of the present invention.
Figure 12A:
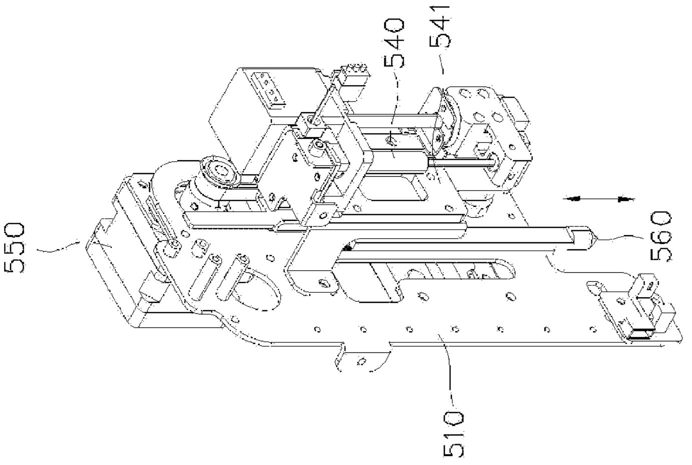

FIG. 10 is a front view illustrating a sampling operation unit according to an embodiment of the present invention. FIGS. 11*a* and 11*b* are perspective and front views illustrating the sampling operation unit without some components (pump unit), respectively, according to an embodiment of the present invention. FIGS. 12*a* and 12*b* are perspective and front views illustrating the sampling operation unit without some components (tip adapter unit), respectively, according to an embodiment of the present invention.

Referring to FIGS. 10, 11*a*, 11*b*, 12*a*, and 12*b*, the sampling operation unit 500 comprises: a main plate 510 assembled with the first guide beam 1043 and horizontally movable along the first guide beam 1043; a tip adapter 520 movable up and down on the main plate 510, and capable of being assembled with a tip 13 provided in the cuvette holder; a seventh driving unit 530 for driving the tip adapter 520 up and down; a pump unit 540 provided on the main plate 510 in parallel with the tip adapter 520 so as to be movable up and down, and for supplying suction or discharge power to the tip adapter 520; and an eighth driving unit 550 for driving the pump unit 540 up and down.

The tip adapter unit includes a tip adapter 520 fixed to the tip adapter block 521. The tip adapter 520 is a hollow member, and its upper end is connected to the pump unit 540 by a flexible tube 522. The tip adapter 520 has a small outer diameter at its lower end and is assembled with the tip 13. In the present embodiment, the tip 13 is a disposable pipette tip having a substantially conical shape and is provided with a protruding part 13*a* on its top, and is assembled with the lower end of the tip adapter 520 by frictional force. On the other hand, the separation process of the tip 13 after use is as follows. The tip adapter 520 and the entire tip 13 move to the top of the tip removal unit 107 (refer to FIG. 3). The tip 13 can be separated from the tip adapter 520 while the tip adapter 520 is raised in a state in which the protruding part 13*a* of the tip 13 is located below the end of the tip removal hole 107*a*. The separated tip 13 is collected in the tip collection container 103 through the tip removal unit 107.

The tip adapter block 521 is vertically driven by a seventh driving unit 530. The seventh driving unit 530 comprises: an electric motor 531; an idle pulley 532 rotatable on the main plate 510; and a belt 533 for connecting a drive shaft 5311 of the electric motor 531 to the idle pulley 532. The tip adapter block 521 is fixed to the belt 533 so that the vertical height of the tip adapter block 521 can be adjusted according to the rotation direction of the belt 533. The main plate 510 may include a third guide beam 5111 that guides the vertical movement of the tip adapter block 521.

Preferably, the main plate 510 is provided at a position corresponding to the mounting height of the tip 13, and further comprises a tip detection unit 512 capable of detecting the presence or absence of the tip 13.

The pump unit 540 is connected to the tip adapter 520 by a flexible tube 522 so as to supply suction or discharge power, and includes a guide block 541 movable up and down on the main plate 510, so that the height of the pump unit 540 can be adjusted up and down by the eighth driving unit 550. The eighth driving unit 550 may be an electric motor that adjusts the height of the guide block 541 via a belt in the same way as the seventh driving unit 530.

The main plate 510 may include a fourth guide beam 5112 for guiding the vertical movement of the guide block 541.

Preferably, the guide block 541 comprises a perforated structure fixed in the vertical direction. Such a perforated structure may be a perforating tip 560 having a pointed shape. The perforating tip 560 perforates the sealing paper that seals the reagent chamber of each cuvette while descending by the driving of the eighth driving unit 550.

Figure 13:
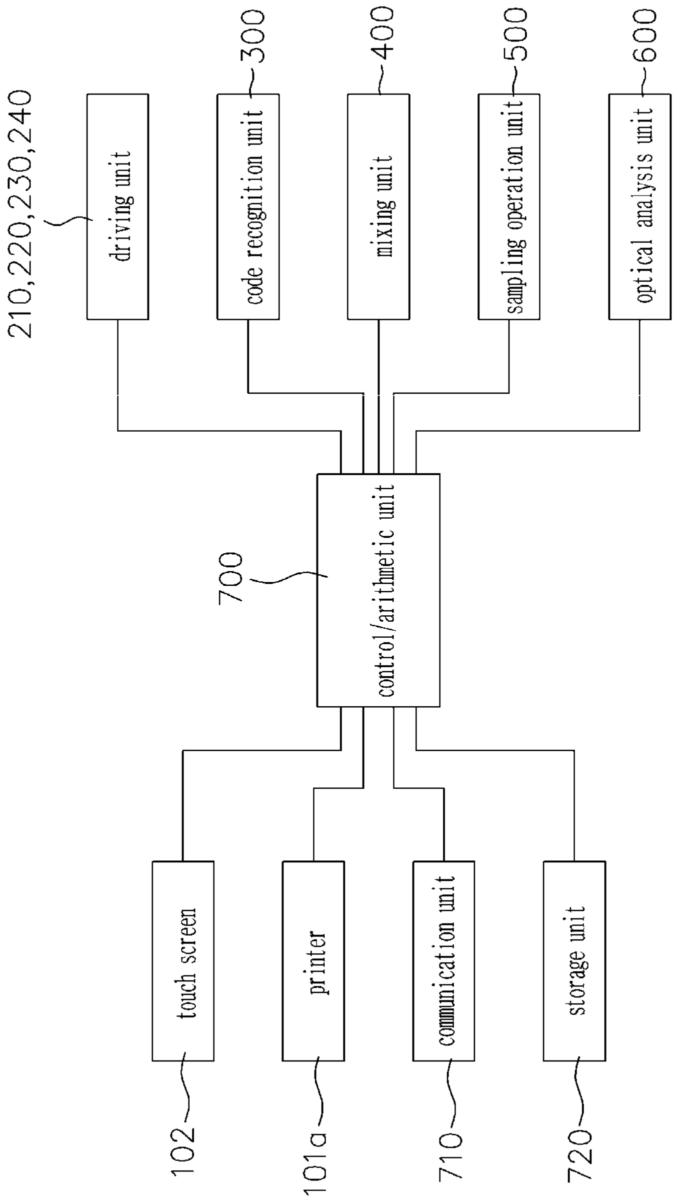
FIG. 13 illustrates the configuration of an automatic in vitro diagnostic apparatus according to an embodiment of the present invention.

FIG. 13 illustrates configuration of an automatic in vitro diagnostic apparatus according to an embodiment of the present invention.

Referring to FIG. 13, the automatic in vitro diagnostic apparatus of this embodiment controls a series of operations for examination according to an algorithm, and comprises a control/arithmetic unit 700 that calculates the detection signal made by the optical analysis unit 600 and derives the measurement result. The result is output to the touch screen 102 or the printer 101*a*. On the other hand, a communication unit 710 and a storage unit 720 are provided. The examination result may be transmitted/received to and from a remote location, such as a hospital system, through the communication unit 710 or stored in a separate storage unit 720. In addition, the control/arithmetic unit 700 may integratedly control the driving units 210, 220, 230 and 240 for driving each driving element, the code recognition unit 300, the mixing unit 400, and the sampling operation unit 500.

The schematic examination process of the automatic in vitro diagnostic apparatus configured as described above will be described.

Referring to FIGS. 3 to 5 and FIG. 13, the cartridge 14 of the item to be measured is inserted into the cuvette holder 10. At this time, whether the cartridge 14 is inserted can be determined by a sensor. By operating an operation button, the cuvette tray 110 moves backward and the barcode is recognized in the slot where the cartridge 14 is inserted, so that it may be determined whether lot information matches the stored item.

Next, when the sample tube 21 containing the sample is inserted into the apparatus through the tube holder 20, the barcode of the tube holder 20 is identified, and information on the sample tube 21 mounted on the tube holder 20 is determined so that as many examinations as the number of samples mounted on the tube holder 20 can be performed. Thereafter, the examination is performed according to the programmed procedure, and the information on the sample taken from the barcode of the sample is stored. Here, when sample information is transmitted from a hospital system, a process of determining whether the sample matches the corresponding sample may be added. If the sample contained in the sample tube 21 is whole blood, a mixing operation may be performed in the mixing unit 400. The sampling operation unit 500 mounts the tip 13, collects a sample, and automatically performs pretreatment (mixing) and dispensing to the cartridge 14. After use, the tip 13 is discharged to the tip collection container 103.

After dispensing is completed, the cartridge 14 waits during a reaction waiting time according to the item information, and is moved to the optical analysis unit 600 so as to be optically scanned. The scanned analog signal is converted into a digital signal to be transmitted to the control/arithmetic unit 700. Next, the control/arithmetic unit 700 analyzes it using an arithmetic formula suitable for the item, and then the examination result is output to the outside.

The present invention described above is not limited by the above-described embodiments and the accompanying drawings. It will be clear to those who have the common knowledge in the technical field to which the present invention pertains, that various substitutions, modifications and changes are possible within the scope without departing from the technical spirit of the present invention.

The invention claimed is:

1. An automatic in vitro diagnostic apparatus comprising:

a base frame;

a cuvette tray movable back and forth on the base frame, for mounting cuvette holders thereon, the cuvette holders accommodating a plurality of cuvettes arranged alongside, wherein one unit set of the cuvette includes at least one open chamber, a reagent chamber, a tip, and a cartridge comprising an assay strip;

a first driving unit comprising a belt for supplying a driving force to the cuvette tray and an electric motor for driving the belt, for moving the cuvette tray back and forth;

a tube tray movable back and forth in parallel with the moving direction of the cuvette tray on the base frame, for mounting tube holders thereon, the tube holders accommodating a plurality of capless tubes containing samples;

a second driving unit comprising a belt for supplying a driving force to the tube tray and an electric motor for driving the belt, for moving the tube tray back and forth;

a buffer tube holder provided between rows of the cuvette holders for accommodating a plurality of buffer tubes, wherein the buffer tube holder is moved back and forth by a separate driving unit;

a sampling operation unit movable left and right on the base frame, for collecting a sample contained in a capless tube, mixing it with a reagent to form a mixed solution, and dropping the mixed solution onto an assay strip provided in a cuvette, the sampling operation unit further comprising a camera module integrated therewith for taking an image while moving horizontally together with the sampling operation unit to identify at least one of cartridge information, tips, presence of a buffer tube and an identity of each patient sample by recognizing code information attached to the capless tubes;

a third driving unit comprising a belt for supplying a driving force to the sampling operation unit and an electric motor for driving the belt, for moving the sampling operation unit left and right;

an optical analysis unit disposed at a rear end of the sampling operation unit, movable left and right on the base frame, for optically analyzing the assay strip with the mixed solution;

a fourth driving unit comprising a belt for supplying a driving force to the optical analysis unit and an electric motor for driving the belt, for moving the optical analysis unit left and right; and a mixing unit for mixing the sample contained in the capless tube, comprising:

a fixing bracket fixed to the base frame, an elevating module supported by the fixing bracket so as to move up and down, a fifth driving unit comprising an electric motor for driving the elevating module up and down, a fixing head supported by the elevating module so as to be able to rotate, and capable of getting fixed closely to an upper opening end of the capless tube, and a sixth driving unit comprising an electric motor provided for the elevating module, for rotating the fixing head; and a control/arithmetic unit for integratedly controlling the first driving unit to the sixth driving unit and the separate driving unit to operate according to a programmed procedure to manage individual matching between the identified patient sample and the cartridge information so that mixing, collection, and analysis are sequentially performed.

2. The automatic in vitro diagnostic apparatus of claim 1, further comprising: a code recognition unit provided adjacent to the tube tray, for recognizing code information attached to a sample tube or a tube holder.

3. The automatic in vitro diagnostic apparatus of claim 1, wherein the elevating module further comprises a linear driving unit for transmitting a driving force generated by the fifth driving unit as linear driving force.

4. The automatic in vitro diagnostic apparatus of claim 1, wherein the fixing head further comprises a contact pad in close contact with an open end of the capless tube.

5. The automatic in vitro diagnostic apparatus of claim 1, wherein the fixing bracket further comprises a guide rail for guiding the vertical movement of the elevating module.

6. The automatic in vitro diagnostic apparatus of claim 5, wherein the elevating module further comprises a linear driving unit for transmitting a driving force generated by the fifth driving unit as linear driving force.

7. The automatic in vitro diagnostic apparatus of claim 1, wherein the sampling operation unit comprises:

a main plate for moving left and right by the third driving unit;

a tip adapter provided on the main plate so as to be movable up and down, and capable of being assembled with a tip provided in a cuvette holder;

a seventh driving unit comprising an electric motor, an idle pulley, and a belt for driving the tip adapter up and down;

a pump unit provided on the main plate in parallel with the tip adapter so as to be movable up and down, and for supplying suction or discharge power to the tip adapter; and an eighth driving unit comprising an electric motor for driving the pump unit up and down.

8. The automatic in vitro diagnostic apparatus of claim 7, wherein the pump unit further comprises a perforated structure fixed in the vertical direction, for perforating sealing paper for sealing a reagent chamber of a cuvette.

* * * * *